(12) United States Patent
Matsumoto

(10) Patent No.: US 10,426,505 B2
(45) Date of Patent: Oct. 1, 2019

(54) HOLLOW STRANDED WIRE LINE FOR MANIPULATION

(71) Applicant: TOKUSEN KOGYO CO., LTD., Ono, Hyogo (JP)

(72) Inventor: Keiji Matsumoto, Ono (JP)

(73) Assignee: TOKUSEN KOGYO CO., LTD., Ono, Hyogo (JP)

( * ) Notice: Subject to any disclaimer, the term of this patent is extended or adjusted under 35 U.S.C. 154(b) by 0 days.

(21) Appl. No.: 15/580,209

(22) PCT Filed: Apr. 22, 2016

(86) PCT No.: PCT/JP2016/062748
§ 371 (c)(1),
(2) Date: Dec. 6, 2017

(87) PCT Pub. No.: WO2017/038154
PCT Pub. Date: Mar. 9, 2017

(65) Prior Publication Data
US 2018/0161053 A1    Jun. 14, 2018

(30) Foreign Application Priority Data

Aug. 31, 2015   (JP) ................................ 2015-170511

(51) Int. Cl.
*A61B 17/32*       (2006.01)
*D07B 1/12*        (2006.01)
(Continued)

(52) U.S. Cl.
CPC .... *A61B 17/32002* (2013.01); *A61B 1/00121* (2013.01); *D07B 1/0673* (2013.01);
(Continued)

(58) Field of Classification Search
CPC ......... A61B 1/00121; D07B 1/12; H01B 5/08
See application file for complete search history.

(56) References Cited

U.S. PATENT DOCUMENTS 4,738,096 A    4/1988  Hatakeyama et al.
5,295,346 A *  3/1994  Bundo ................. B60C 9/0007
                                              152/451

(Continued)

FOREIGN PATENT DOCUMENTS

FR    2533744 A1    3/1984
JP    1-62396 U     4/1989
(Continued)

*Primary Examiner* — Hoa C Nguyen
*Assistant Examiner* — Amol H Patel
(74) *Attorney, Agent, or Firm* — Dickinson Wright PLLC

(57) ABSTRACT

[Object] A hollow stranded wire line, for manipulation, having an excellent torque transmittability is provided.
[Solution] A hollow stranded wire line 2 for manipulation is a hollow stranded wire line 2 that is advantageously used as a stranded wire line for manipulation in a medical instrument, and a side wire 4 or a side strand which is an outermost layer has a forming rate that is greater than 100% and not greater than 110%. The side wire 4 or the side strand having been formed has a spiral shape in which a flatness that is an aspect ratio obtained by a major axis being divided by a minor axis is preferably not less than 1.01 and preferably not greater than 1.10.

3 Claims, 5 Drawing Sheets

(51) Int. Cl.
  *A61B 1/00* (2006.01)
  *D07B 1/06* (2006.01)
  *F16C 1/02* (2006.01)
  *F16C 1/20* (2006.01)
  *A61B 17/00* (2006.01)
  *A61M 25/09* (2006.01)

(52) U.S. Cl.
  CPC ............ *D07B 1/0693* (2013.01); *D07B 1/12* (2013.01); *F16C 1/02* (2013.01); *F16C 1/20* (2013.01); *A61B 17/00* (2013.01); *A61M 2025/09108* (2013.01); *A61M 2025/09133* (2013.01); *A61M 2025/09191* (2013.01); *D07B 1/0633* (2013.01); *D07B 1/0646* (2013.01); *D07B 2201/204* (2013.01); *D07B 2201/2008* (2013.01); *D07B 2201/2021* (2013.01); *D07B 2201/2022* (2013.01); *D07B 2201/2039* (2013.01); *D07B 2201/2063* (2013.01); *D07B 2205/3028* (2013.01); *D07B 2205/3032* (2013.01); *D07B 2207/4063* (2013.01); *D07B 2207/4072* (2013.01); *D07B 2501/2084* (2013.01)

(56) References Cited

U.S. PATENT DOCUMENTS

| | | |
|---|---|---|
| 5,766,184 A | 6/1998 | Matsuno et al. |
| 2002/0151823 A1 | 10/2002 | Miyata et al. |
| 2008/0051694 A1* | 2/2008 | Kato .................. A61B 1/00071 604/22 |

FOREIGN PATENT DOCUMENTS

| | | | | |
|---|---|---|---|---|
| JP | 5-230783 A | | 9/1993 | |
| JP | 06-063142 A | | 3/1994 | |
| JP | 8-126648 A | | 5/1996 | |
| JP | 2003-052831 A | | 2/2003 | |
| JP | 2006-283259 A | | 10/2006 | |
| JP | 2008-048850 A | | 3/2008 | |
| JP | 2008-155052 A | | 7/2008 | |
| JP | 2011-006803 A | | 1/2011 | |
| JP | 2011006803 A | * | 1/2011 | ................ F16C 1/02 |
| JP | 2011-202321 A | | 10/2011 | |
| JP | 2012-082530 A | | 4/2012 | |

* cited by examiner

HOLLOW STRANDED WIRE LINE FOR MANIPULATION

TECHNICAL FIELD

The present invention relates to hollow stranded wire lines, for manipulation, which can be used also for, for example, medical instruments.

BACKGROUND ART

To date, a medical instrument (also referred to as a medical device) in which a manipulation wire rope or the like is used as one of components, has been known. As such a medical instrument, for example, an endoscope treatment instrument disclosed in JPH8-126648 is known. In the endoscope treatment instrument, an operation unit being held by hand and a treatment unit provided at its leading end are connected by a manipulation wire rope having torque transmittability. An operator inserts the treatment unit into a body cavity of a patient and operates the operation unit, whereby an operating force thereof is transmitted to the treatment unit by the manipulation wire rope. The manipulation wire rope allows a pushing force, a pulling force, and a rotational force (torque) to be transmitted from the operation unit to the treatment unit. By the transmitted force, a portion, of a body, to be treated can be subjected to medical treatment.

The manipulation wire rope is required to have not only transmittability of pushing and pulling force, but also an excellent torque transmittability (rotation followability) according to application of the manipulation wire rope. In a case where a torque transmittability or the like of the manipulation wire rope is insufficient, an operation of the operation unit is not reproduced by the treatment unit. Furthermore, particularly in the field of medical devices, the manipulation wire rope is required to have flexibility according to the diameter of the medical device being reduced.

JPH6-63142 discloses a coil-shaped pipe used as a catheter for diagnosis and treatment. The pipe is formed by a metal wire material being wound into a coil. In the pipe, the coils adjacent to each other are in pressure contact with each other by an initial restoring force due to forming of the coil shape. This catheter is also required to have flexibility, pushability included in transmittability of pushing and pulling force, torque transmittability, and the like, as described above.

CITATION LIST

Patent Literature

Patent Literature 1: JPH8-126648
Patent Literature 2: JPH6-63142

SUMMARY OF THE INVENTION

Problems to be Solved by the Invention

The present invention is made in view of the aforementioned circumstances, and an object of the present invention is to provide a hollow stranded wire line, for manipulation, having an excellent torque transmittability.

Solution to the Problems

A hollow stranded wire line for manipulation according to the present invention has a side wire or a side strand which is an outermost layer, the side wire or the side strand having a forming rate that is greater than 100% and not greater than 110%.

Preferably, the side wire or the side strand having been formed has a spiral shape in which a flatness that is an aspect ratio obtained by a major axis being divided by a minor axis is not less than 1.01 and not greater than 1.10.

Preferably, the forming rate is not less than 101% and not greater than 105%.

Preferably, the flatness is not less than 1.01 and not greater than 1.05.

Advantageous Effects of the Invention

The hollow stranded wire line for manipulation according to the present invention has an excellent torque transmittability.

DESCRIPTION OF EMBODIMENTS

The following will describe in detail the present invention based on preferred embodiments with reference where appropriate to the accompanying drawing.

Figure 1:
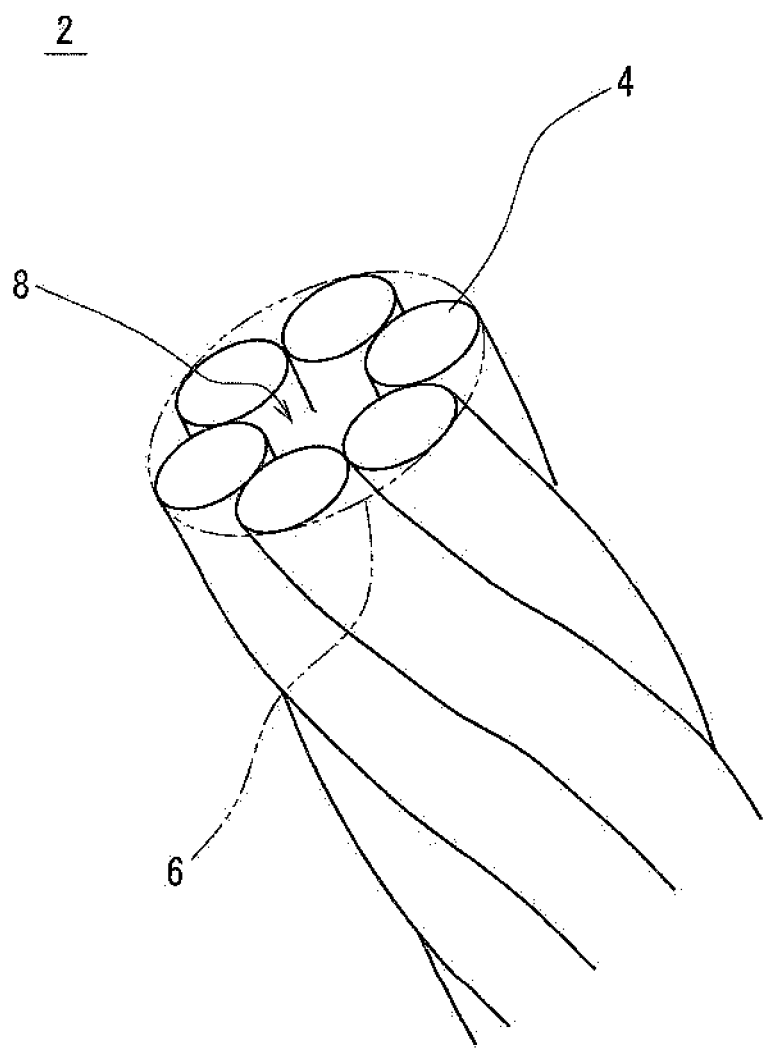
FIG. 1 is a perspective view of a part of a hollow stranded wire line for manipulation according to one embodiment of the present invention.
Figure 2:
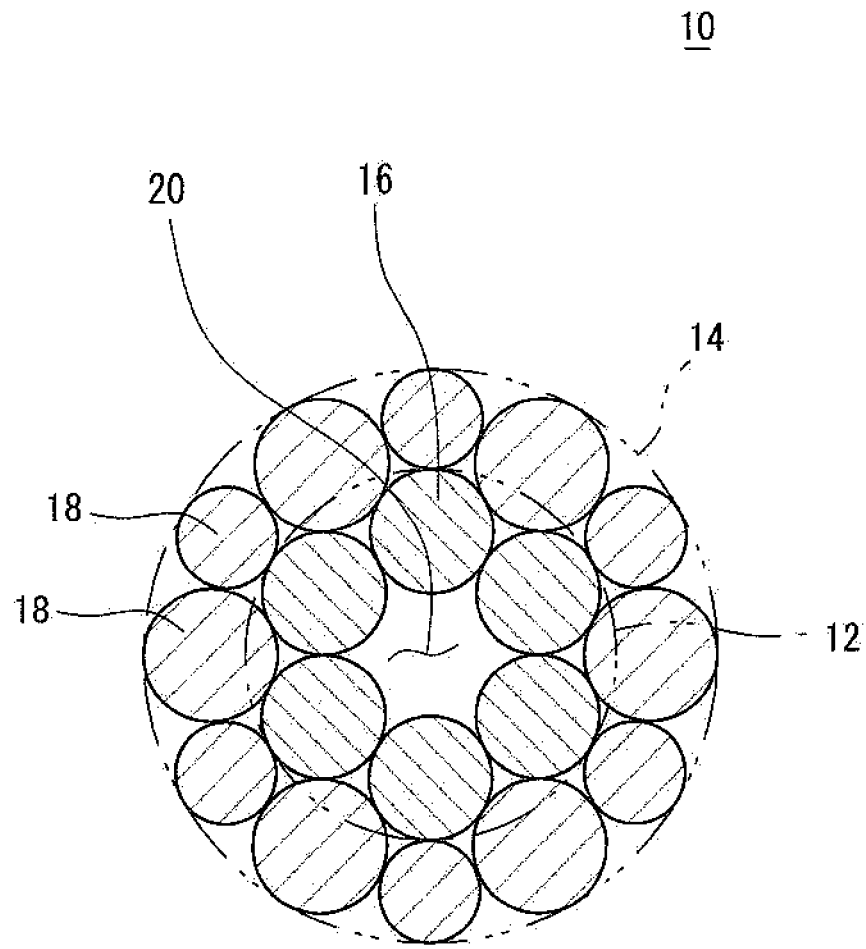
FIG. 2 is a transverse cross-sectional view of a hollow stranded wire line for manipulation according to another embodiment of the present invention.

FIG. 1 and FIG. 2 illustrate hollow stranded wire lines for manipulation (hereinafter, each of which is simply referred to also as hollow stranded wire line) according to different embodiments of the present invention. Each of the hollow stranded wire lines 2, 10 has a structure in which a plurality of wires are stranded. However, the present invention is not limited to the structures of the embodiments shown in FIG. 1 and FIG. 2.

The hollow stranded wire line 2 shown in FIG. 1 has a layer 6 formed from six wires 4, that is, has a stranded structure having one layer formed from six filament wires. The hollow stranded wire line 2 has a tunnel-shaped internal space 8.

The hollow stranded wire line 10 shown in FIG. 2 has two layers that are a lower layer (inner layer) 12 and an upper layer (outer layer) 14. The lower layer 12 has a stranded structure, having six wires 16, which has one layer formed from six filament wires. The upper layer 14 has a stranded structure, having 12 wires 18, which has one layer formed from 12 filament wires. The hollow stranded wire line 10 has a tunnel-shaped internal space 20. Side wires 18 having different diameters are used for the hollow stranded wire line 10 such that the transverse cross-sectional shape becomes close to a circular shape. However, the side wires 18 are not limited to such a structure, and all the side wires 18 may have an equal diameter.

The wire 4, 18 which forms the outermost layer is also called side wire. In a case where the outermost layer is formed by not a wire but a strand, the strand is also called side strand. As a stranded structure for the hollow strand wire line for manipulation in a medical instrument, the structures of the hollow stranded wire lines 2, 10 are appropriate. However, the stranded structure is not limited to the structures of the hollow stranded wire lines 2, 10.

The hollow stranded wire line can be manufactured by using a stranding machine for wire ropes in a manner similar to a stranding manner for a wire rope. In this case, the following two manufacturing methods can be used. The first method is a method in which a preformed side wire, side strand, or the like is stranded along a circumference without inserting a core wire and a core strand. In the stranding process, the hollow stranded wire line is formed. Subsequently, the hollow stranded wire line is subjected to post heat treatment. The second method is a method in which a preformed side wire, side strand, or the like is stranded along a circumference in a state where a core wire or a core strand is inserted. In the stranding process, a wire rope is formed. Subsequently, the wire rope is subjected to post heat treatment. After the wire rope is cut so as to have a predetermined length, the core wire or the core strand is extracted, to obtain the hollow stranded wire line.

A process for manufacturing the hollow stranded wire line will be briefly described below. Firstly, wires of the hollow stranded wire line are each adjusted in the wire drawing process step such that a required tensile strength can be obtained. Then, preforming is performed for the side wire or the side strand by a preformer in the wire stranding process step such that required forming rate and flatness can be obtained. In particular, the preforming is performed such that the spiral of the side wire or the side strand has a flattened transverse cross-section. The wires or strands are stranded by the stranding machine. In the case of a stranded wire line which does not include a core wire or a core strand (FIG. 1, FIG. 2), a hollow stranded wire line is formed in the stranding process step.

In the post heat treatment process step for the hollow stranded wire line, not batch processing but continuous processing is performed. Specifically, the hollow stranded wire line, to be processed, which passes through a heat treatment furnace is tensioned at an inlet and an outlet of the heat treatment furnace. Thus, the straightness of the hollow stranded wire line is improved. Further, the forming rate and the flatness of the side wire or the side strand are determined. Thus, the hollow stranded wire line is completed.

Figure 3:
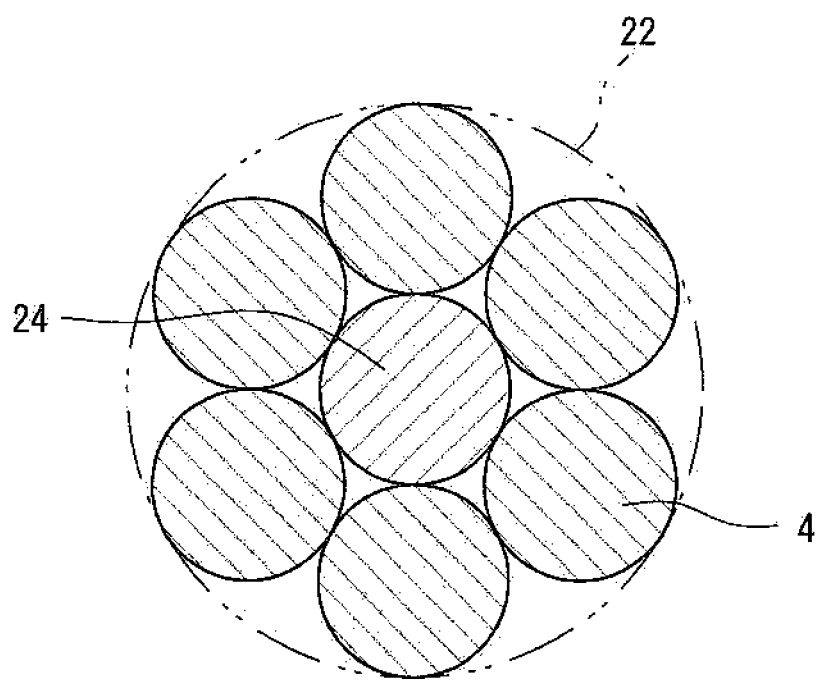
FIG. 3 is a transverse cross-sectional view of an example of a wire rope in a process of manufacturing the hollow stranded wire line for manipulation in FIG. 1.

Meanwhile, in this manufacturing process, in a case where the stranded wire line includes a core wire or a core strand, a wire rope is completed. For example, as shown in FIG. 3, a 1+6 layer stranded wire rope 22 having one core wire 24, and six side wires 4 which form an outermost layer, is completed. Then, as described above, the wire rope 22 is cut so as to have a predetermined length, and the core wire 24 is extracted, whereby the hollow stranded wire line 2 as shown in, for example, FIG. 1 is completed.

The hollow stranded wire lines 2, 10 of the embodiments can be used for a medical instrument. The hollow stranded wire line is attached to a medical instrument for manipulation such that, for example, the proximal end portion of the hollow stranded wire line is connected to an operation unit, being held by hand, of the medical instrument, and the leading end portion of the hollow stranded wire line is connected to a treatment unit. Torque and pushing and pulling force applied to the proximal end portion are transmitted to the leading end portion, and the treatment unit is allowed to perform a treatment operation.

In the present embodiment, the wire of the hollow stranded wire line 2, 10 is formed from an austenitic stainless steel such as SUS304 and SUS316, a nickel-titanium alloy, or the like. Needless to say, the material of the wire is not limited to such a material. The tensile strength of the material of the wire is preferably not less than 2000 MPa, more preferably not less than 2500 MPa, and particularly preferably not less than 2800 MPa.

A forming rate of the side wire 4, 18 or the side strand which is the outermost layer of the hollow stranded wire line 2, 10, is greater than 100% and not greater than 110%. The forming rate is calculated in such a manner that the diameter (waviness diameter) of a spiral shape of the side wire or the side strand in a state where the hollow stranded wire line is disassembled (disentangled), is divided by an actually measured outer diameter of the hollow stranded wire line, and the obtained value is represented by a percentage as the forming rate. When the forming rate is in the above-described range, the hollow stranded wire line becomes flexible and is easily bent. Further, friction between the side wires or between the side strands is increased, thereby reducing energy loss in transmission of rotation of the hollow stranded wire line. Further, in a case where the hollow stranded wire line has a plurality of layers as illustrated in FIG. 2, friction between an inner layer and an outer layer is reduced, thereby further reducing energy loss in transmission of rotation of the hollow stranded wire line. It has been found that, by this action, transmission of rotational force from the proximal end to the leading end is facilitated, and torque transmittability is improved. Further, in a case where the forming rate is in the above-described range, also when a subject to be stranded does not include a core wire or a core strand, the side wire is less likely to be inserted into the internal space in the stranding process step using the stranding machine.

However, when the forming rate is not greater than 100%, a force toward the center of the hollow stranded wire line constantly acts on the side wire. Therefore, when the hollow stranded wire line is bent, the transverse cross-section tends to be deformed into an ellipsoidal shape. As a result, transmission of rotation of the hollow stranded wire line may be hindered. Further, in the case of the hollow stranded wire line having a plurality of layers as illustrated in FIG. 2, a friction between the inner layer and the outer layer is increased, and energy loss in transmission of rotation of the hollow stranded wire line may be thus increased. Further, in a case where a subject to be stranded does not include a core wire or a core strand, the side wire may be inserted into the internal space in the stranding process step. Meanwhile, when the forming rate is greater than 110%, a so-called open structure in which a gap is generated among the wires may be caused, and the diameter of the hollow stranded wire line may not be obtained as desired. In this viewpoint, the forming rate is preferably not less than 101% and preferably not greater than 105%.

The spiral of the side wire or the side strand is not completely circular but ellipsoidal or oval in some cases. In these cases, the spiral is a so-called flattened spiral. In this case, as the waviness diameter by which the forming rate is determined, the major axis among the major axis and the minor axis is used. Also when the major axis is used as the waviness diameter, the hollow stranded wire line 2, 10 is formed such that the forming rate is not greater than 110%. Further, if the minor axis is used as the waviness diameter, the hollow stranded wire line 2, 10 is formed such that the forming rate is greater than 100%.

In the side wire 4, 18 or the side strand which is the outermost layer of the hollow stranded wire line 2, 10, the flatness (also referred to as aspect ratio) is preferably not less than 1.01 and preferably not greater than 1.10. The flatness represents an aspect ratio, of the above-described flattened spiral of the disentangled side wire or side strand, obtained by dividing the major axis by the minor axis. An example of a method for measuring the diameter of the spiral will be described below. On a projector, the disentangled side wire or side strand is rotated around the center axis thereof. In this process, the diameters of the spiral are measured at any plurality of angular positions (for example, five positions). The plurality of angular positions are preferably spaced from each other at equiangular intervals. The greatest value among the plurality of measured values is determined as the major axis. The diameter of the spiral which is measured in the direction obtained by 90° phase rotation around the center axis of the side wire or the side strand being performed from the direction in which the major axis is measured, is determined as the minor axis. In the disentangled side wire or side strand, a plurality of spirals are formed continuously along the axial direction thereof. Therefore, as each diameter in the 90° intersecting direction, an average of a plurality of measured values (for example, at any 10 positions) is adopted.

When the flatness is not less than 1.01, friction between the side wires or between the side strands is further increased, so that an effect of further reducing energy loss in transmission of rotation of the hollow stranded wire line is obtained. However, when the flatness is less than 1.01, this advantageous effect cannot be expected. Further, in the case of the hollow stranded wire line having a plurality of layers as shown in FIG. 2, when the flatness is less than 1.01, friction between an inner layer and an outer layer is increased, and energy loss in transmission of rotation of the hollow stranded wire line may be thus increased. Meanwhile, when the flatness is greater than 1.10, a so-called open structure is caused, and the hollow stranded wire line may be difficult to stably manufacture. In this viewpoint, the flatness is preferably not less than 1.01 and preferably not greater than 1.05.

As described above, when the forming rate of the side wire or the side strand is in the above-described range, flexibility, bendability, and transmittability of rotational force in the hollow stranded wire line are improved. In addition thereto, it has been found that, when the flatness is in the above-described range, flexibility, bendability, and transmittability of rotational force in the hollow stranded wire line are further improved.

A strand angle of the side wire 4, 18 or the side strand of the hollow stranded wire line 2, 10 is preferably not less than 15°. The hollow stranded wire line in which the strand angle is not less than 15° becomes more flexible and is easily bent. The strand angle is an angle between the wire or the strand, and the center axis of the hollow stranded wire line or the strand. In the description herein, the strand angle is an angle between the side wire or the side strand, and the center axis of the hollow stranded wire line.

EXAMPLES

Hereinafter, effects of the present invention will become apparent according to examples. However, the present invention should not be restrictively construed based on the description of examples.

Examples 1 to 9

Hollow stranded wire lines, for manipulation, of examples 1 to 9 each having the structure shown in FIG. 1 were obtained. Each of the hollow stranded wire lines was a hollow stranded wire line of wires for a medical device. A material of each of the wires was SUS304 austenitic stainless steel. The outer diameter (cord diameter) of the hollow stranded wire line was 0.7 mm. Firstly, a wire rope was manufactured, and a core wire was extracted from the wire rope, to manufacture the hollow stranded wire line. The outer diameter of the core wire of the wire rope during manufacturing of the hollow stranded wire line was 0.25 mm. The outer diameter of the side wire was 0.23 mm. The side wire and the core wire each had the tensile strength of 2800 MPa. Each hollow stranded wire line had a stranded structure obtained by a core wire being extracted from the 1+6 layer stranded rope. A stranding pitch in each hollow stranded wire line was 5.5 mm. The temperature in the heat treatment for the hollow stranded wire line of each of examples 1 to 9 was 500° C. The forming rate and the flatness of the side wire of the hollow stranded wire line of each of examples 1 to 9 were as indicated in Table 1 and Table 2.

Comparative Example 1

A hollow stranded wire line, for manipulation, of comparative example 1 was obtained in the same manner as in example 1 except that the forming rate and the flatness were as indicated in Table 2, and the cord diameter was much greater than 0.7 mm. As indicated in Table 2, the forming rate of the hollow stranded wire line of comparative example 1 was 115%, and a so-called open structure in which multiple gaps were generated among the wires, was thus caused. Therefore, the cord diameter was much greater than 0.7 mm. Such a hollow stranded wire line of comparative example 1 was not suitable as a hollow stranded wire line for manipulation in a medical device, and it was determined that this hollow stranded wire line was not able to be used as a hollow stranded wire line for manipulation in a medical device.

Comparative Example 2

Comparative example 2 was a hollow stranded wire line for manipulation according to conventional art. The hollow stranded wire line, for manipulation, of comparative example 2 was the same as in example 1 except that the forming rate and the flatness were as indicated in Table 2. The side wire of the hollow stranded wire line of comparative example 2 was not formed so as to be flattened.

TABLE 1

| | Evaluation of torque transmittability | | | | | |
|---|---|---|---|---|---|---|
| | Ex. 1 | Ex. 2 | Ex. 3 | Ex. 4 | Ex. 5 | Ex. 6 |
| Forming rate (%) | 100.5 | 105 | 101 | 101 | 101 | 101 |
| Flatness | 1.01 | 1.01 | 1.00 | 1.005 | 1.05 | 1.01 |
| Torque transmittability (index) | 59.0 | 30.3 | 56.5 | 45.2 | 21.5 | 19.7 |

TABLE 2

Evaluation of torque transmittability

|  | Ex. 7 | Ex. 8 | Ex. 9 | Comp. Ex. 1 | Comp. Ex. 2 |
|---|---|---|---|---|---|
| Forming rate (%) | 102 | 101 | 110 | 115 | 99 |
| Flatness | 1.02 | 1.10 | 1.01 | 1.01 | 1.00 |
| Torque transmittability (index) | 17.3 | 38.9 | 47.0 | Not usable | 100 |

[Evaluation of Torque Transmittability]

Torque transmittability is evaluated on the basis of difference, between a rotation angle on the proximal end side (corresponding to the operation unit of a medical instrument) and a rotation angle on the leading end side (corresponding to the treatment unit of the medical instrument), obtained when the proximal end side portion of each hollow stranded wire line was rotated. For the hollow stranded wire line of each of examples and comparative examples, the following torque transmittability evaluation test was performed.

Figure 4:
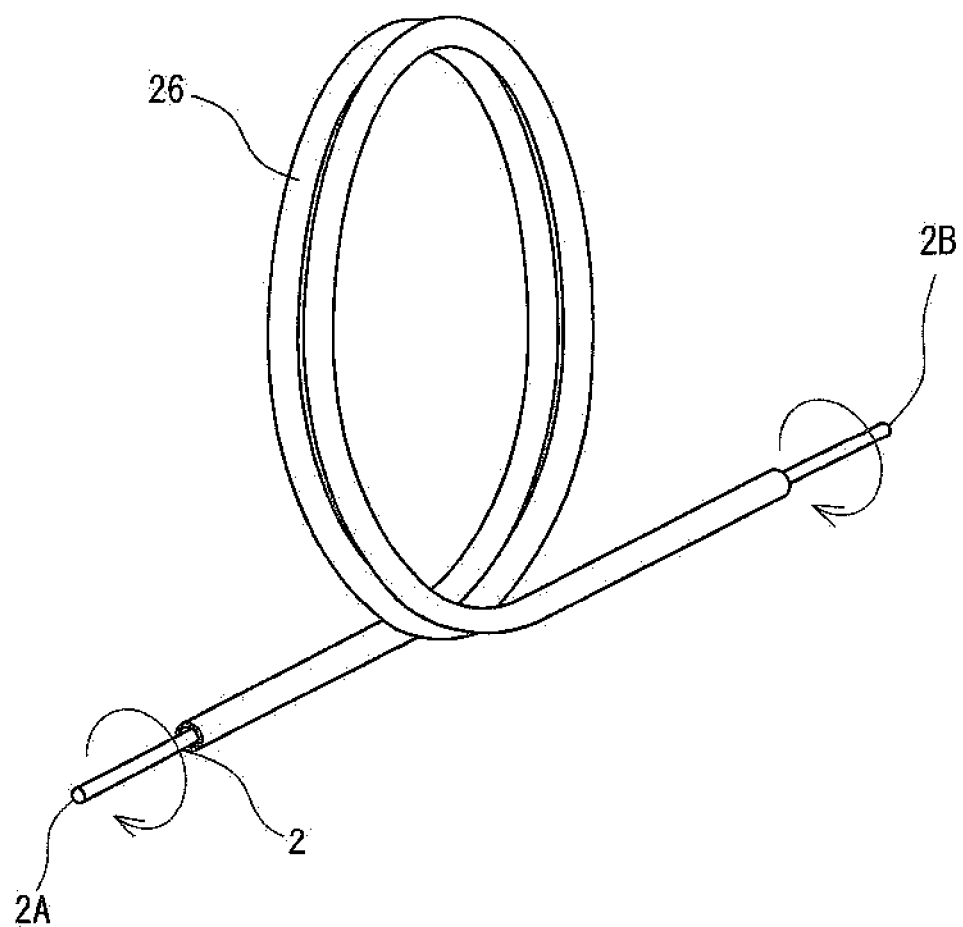
FIG. 4 is a perspective view illustrating an outline of a torque transmittability evaluation testing method for a hollow stranded wire line for manipulation.

A dual spiral having the diameter of 200 mm was formed in the hollow stranded wire line of each of examples 1 to 9 and comparative examples 1, 2. As shown in FIG. 4, the dual spiral was formed by using a small-diameter pipe 26 which had a dual spiral shape having the diameter of 200 mm so as to be straight on both end sides. For example, a hollow stranded wire line 2 to be tested was inserted into the small-diameter pipe 26. A rotational force around the center axis was applied to a proximal end side 2A portion of the hollow stranded wire line 2 to be tested, in a state where the hollow stranded wire line 2 to be tested was inserted in the small-diameter pipe 26. While the rotational force was applied, a rotation angle on the proximal end side 2A of the hollow stranded wire line 2 and a rotation angle on a leading end side 2B thereof were simultaneously measured.

Figure 5:
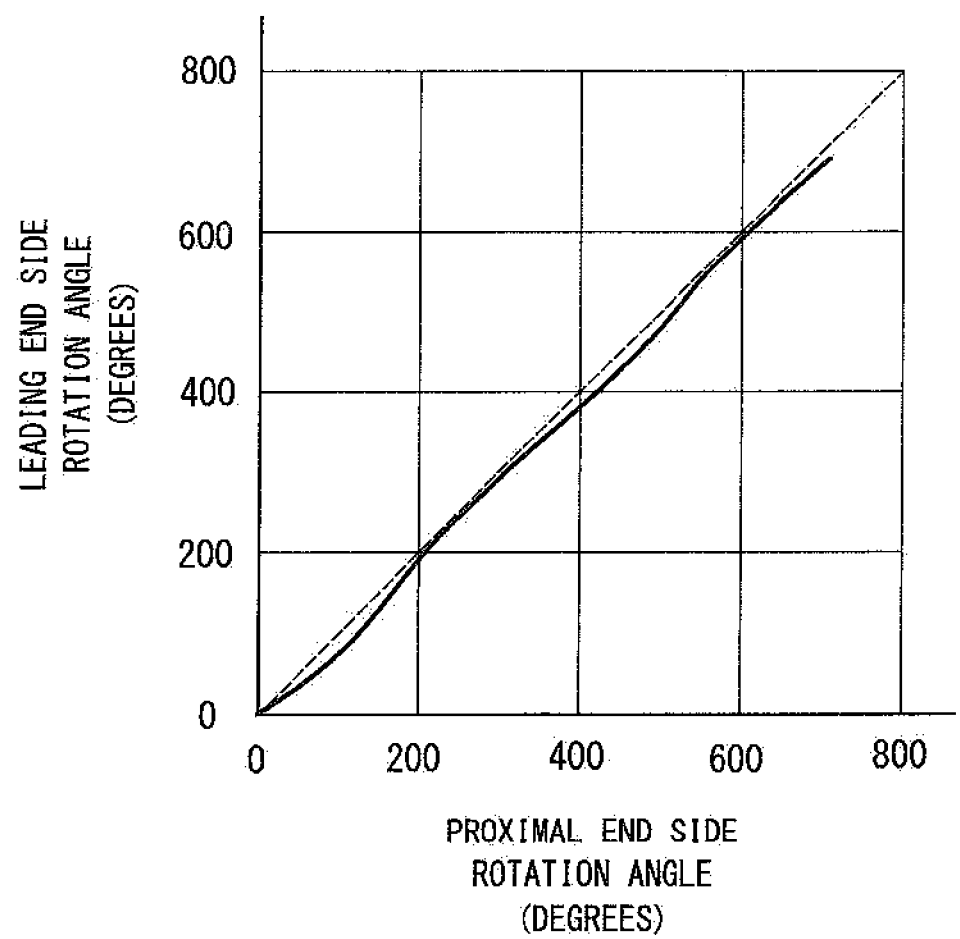
FIG. 5 shows a graph in which a rotation angle on a proximal end side of a hollow stranded wire line for manipulation, and a rotation angle on the leading end side thereof at the same point of time are associated with each other.

FIG. 5 shows a graph in which the rotation angle on the proximal end side 2A of the hollow stranded wire line and the rotation angle on the leading end side 2B thereof at the same point of time are associated with each other. In other words, FIG. 5 is a graph indicating a relationship between an input rotation angle and an output rotation angle in the hollow stranded wire line for manipulation. The unit of the angle is degree)(°). In the graph, a broken line that extends from the originating point of 0° so as to be tilted by 45° relative to the horizontal axis and the vertical axis represents a straight line that indicates that difference between the rotation angle on the proximal end side 2A and the rotation angle on the leading end side 2B is zero in a range of all the measured angles (range in which the input rotation angle is from 0° to about 720°). The difference, to be evaluated for the hollow stranded wire line to be tested, between the rotation angle on the proximal end side 2A and the rotation angle on the leading end side 2B is represented as difference in the vertical axis direction between the 45° titled straight line and the measured value curve in the drawing. The difference in the rotation angle corresponds to the rotation angle on the proximal end side. In the drawing, for easy understanding, the difference in the rotation angle is indicated so as to be greater than the actual one. In the range in which the input rotation angle is from 0° to 720°, the greatest angular difference among the measured differences in the rotation angle is evaluated.

The greatest angular difference in the hollow stranded wire line of each of examples 1 to 9 and comparative examples 1, 2 is indicated in Table 1 and Table 2 as an index with the greatest angular difference of comparative example 2 being 100. The less the greatest angular difference is, the less the value of the index is and the more excellent the torque transmittability is.

As indicated in Table 1 and Table 2, the evaluation result clearly indicates that the present invention is superior.

INDUSTRIAL APPLICABILITY

The hollow stranded wire line for manipulation according to the present invention is advantageously used as a hollow stranded wire line for manipulation in a medical instrument.

DESCRIPTION OF THE REFERENCE CHARACTERS 2, 10 . . . hollow stranded wire line for manipulation
14, 18 . . . side wire
6 . . . layer
8, 20 . . . internal space
12 . . . lower layer (inner layer)
14 . . . upper layer (outer layer)
16 . . . wire
22 . . . wire rope
24 . . . core wire
26 . . . small-diameter pipe

The invention claimed is:

1. A hollow stranded wire line for manipulation, the hollow stranded wire line comprising a side wire or a side strand which is an outermost layer, the side wire or the side strand having a forming rate that is greater than 100% and not greater than 110%, wherein
in a state where the hollow stranded wire line is disentangled, the side wire or the side strand having been formed has a flattened spiral shape, and wherein the side wire or the side strand has a spiral shape with a flatness having an aspect ratio obtained by a major axis being divided by a minor axis of not less than 1.01 and not greater than 1.10.

2. The hollow stranded wire line, for manipulation according to claim 1, wherein the forming rate is not less than 101% and not greater than 105%.

3. The hollow stranded wire line, for manipulation, according to claim 1, wherein the flatness is not less than 1.01 and not greater than 1.05.

* * * * *